United States Patent
DiRocco et al.

(10) Patent No.: US 10,131,674 B2
(45) Date of Patent: Nov. 20, 2018

(54) PROCESS FOR PREPARING SUBSTITUTED INDOLE COMPOUNDS

(71) Applicant: Merck Sharp & Dohme Corp., Rahway, NJ (US)

(72) Inventors: Daniel A. DiRocco, Lebanon, NJ (US); Ian Davies, Princeton, NJ (US); Feng Peng, Edison, NJ (US); Mark McLaughlin, Summit, NJ (US); Louis-Charles Campeau, Morris Plains, NJ (US); Yingju Xu, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/524,872

(22) PCT Filed: Nov. 5, 2015

(86) PCT No.: PCT/US2015/059129
§ 371 (c)(1),
(2) Date: May 5, 2017

(87) PCT Pub. No.: WO2016/073659
PCT Pub. Date: May 12, 2016

(65) Prior Publication Data
US 2017/0334926 A1 Nov. 23, 2017

Related U.S. Application Data

(60) Provisional application No. 62/076,255, filed on Nov. 6, 2014.

(51) Int. Cl.
  C07D 498/04 (2006.01)
  B01J 31/18 (2006.01)
  B01J 35/00 (2006.01)

(52) U.S. Cl.
  CPC .......... *C07D 498/04* (2013.01); *B01J 31/181* (2013.01); *B01J 35/004* (2013.01); *B01J 2231/766* (2013.01); *B01J 2531/827* (2013.01)

(58) Field of Classification Search
  CPC .................................................. C07D 498/04
  USPC ........................................................ 544/89
  See application file for complete search history.

(56) References Cited

PUBLICATIONS

Chakraborty, S., et al, "A Molecular Iron Catalyst for the Acceptorless Dehydrogenation and Hydrogenation of N-Heterocycles", J. Am. Chem. Soc., 2014, pp. 8564-8567, vol. 136.
Chelucci, G., et al, "Synthesis and Application in Asymmetric Copper(I)-Catalyzed Allylic Oxidation of a New Chiral 1,10-Phenanthroline Derived From Pinene", Tetrahedron Letters, 2002, pp. 3601-3604, vol. 43.
Georgopoulos, M., et al, "Cage Escape Yields in the Quencing of *Ru(bpy)32+ by Methylviologen. Prsence of Triethanolamine as a Sacrificial Electron Donor", J. Phys. Chem., 1991, pp. 7717-7721, vol. 95.
Hara, T., et al, "Highly Efficient Dehydrogenation of Indolines to Indoles Using Hydroxyapatitie-Bound Pd Catalyst", Tetrahedron Letters, 2003, pp. 6207-6210, vol. 44.
International Search Report and Written Opinion for PCT/US2015/059129, dated Mar. 18, 2016, 13 pages.
Lowry, M.S., et al, "Single-Layer Electroluminescent Devices and Photoinduced Hydroven Production from an Ionic Iridium(III) Complex", Chem. Mater, 2005, pp. 5712-5719, vol. 17.
Sekar, G. et al, "Asymmetric Kharasch Reaction: Catalytic Enantioselective Allylic Oxidation of Olefins Using Chiral Pyridine Bis(diphenyloxazoline)-Copper Complexes and tert-Butyl Perbenzoate", J. Org. Chem., 1998, pp. 2961-2967, vol. 63.
Tilstam, U., et al, "A Mild and Efficient Dehydrogenation of Indolines", Tetrahedron Letters, 2001, pp. 5385-5387, vol. 42.

*Primary Examiner* — Kahsay Habte
(74) *Attorney, Agent, or Firm* — Jeffrey P. Bergman; Catherine D. Fitch

(57) ABSTRACT

The present invention is directed to a process for preparing Substituted Indole Compounds of Formula (I): wherein $R^1$, $R^2$, $R^3$ and $R^4$ are as defined herein. These indole compounds are useful as synthetic intermediates for making inhibitors of HCV NS5A.

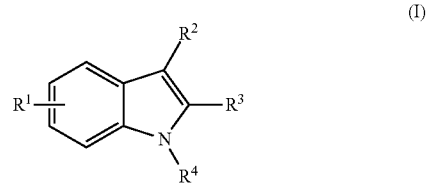

(I)

13 Claims, No Drawings

PROCESS FOR PREPARING SUBSTITUTED INDOLE COMPOUNDS

CROSS-REFERENCE TO RELATED APPLICATIONS

This application is the national stage application under 35 U.S.C. 371 of International Patent Application No. PCT/US15/059129, filed Nov. 5, 2015, which claims priority to U.S. Provisional Patent Application No. 62/076,255, filed Nov. 6, 2014. Each of the aforementioned applications is incorporated by reference in its entirety.

FIELD OF THE INVENTION

The present invention is directed to a process useful for making Substituted Indole Compounds. Such indole compounds are useful as synthetic intermediates for making inhibitors of HCV NS5A.

BACKGROUND OF THE INVENTION

Various substituted tetracyclic heterocyclic compounds are inhibitors of the HCV NS5A enzyme. Included in these heterocycles are indole-type compounds related to Compound A, as defined and described below. These compounds and pharmaceutically acceptable salts thereof are useful in the treatment or prophylaxis of infection by HCV and in the treatment, prophylaxis, or delay in the onset or progression of HCV infection. Representative tetracyclic heterocyclic compounds that are useful for treating HCV infection are described, for example, in US Patent Publication No. US20120083483. Among the compounds disclosed in US20120083483 is dimethyl ((2S,2'S)-((2S,2'S)-2,2'-(5,5'-((S)-6-phenyl-6H-benzo[5,6][1,3]oxazino[3,4-a]indole-3,10-diyl)bis(1H-imidazole-5,2-diyl))bis(pyrrolidine-2,1-diyl))bis(3-methyl-1-oxobutane-2,1-diyl))dicarbamate, hereinafter referred to as Compound A. Compound A is a known inhibitor of HCV NS5A. The structure of Compound A is as follows:

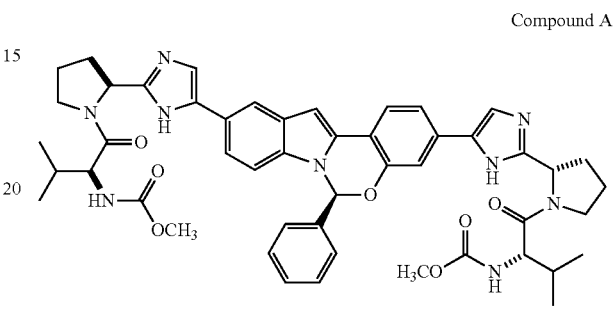

Compound A

US Patent Publication No. US20120083483 discloses methodology that can be employed to prepare Compound A and related tetracyclic HCV NS5A inhibitors. This general methodology is illustrated immediately below:

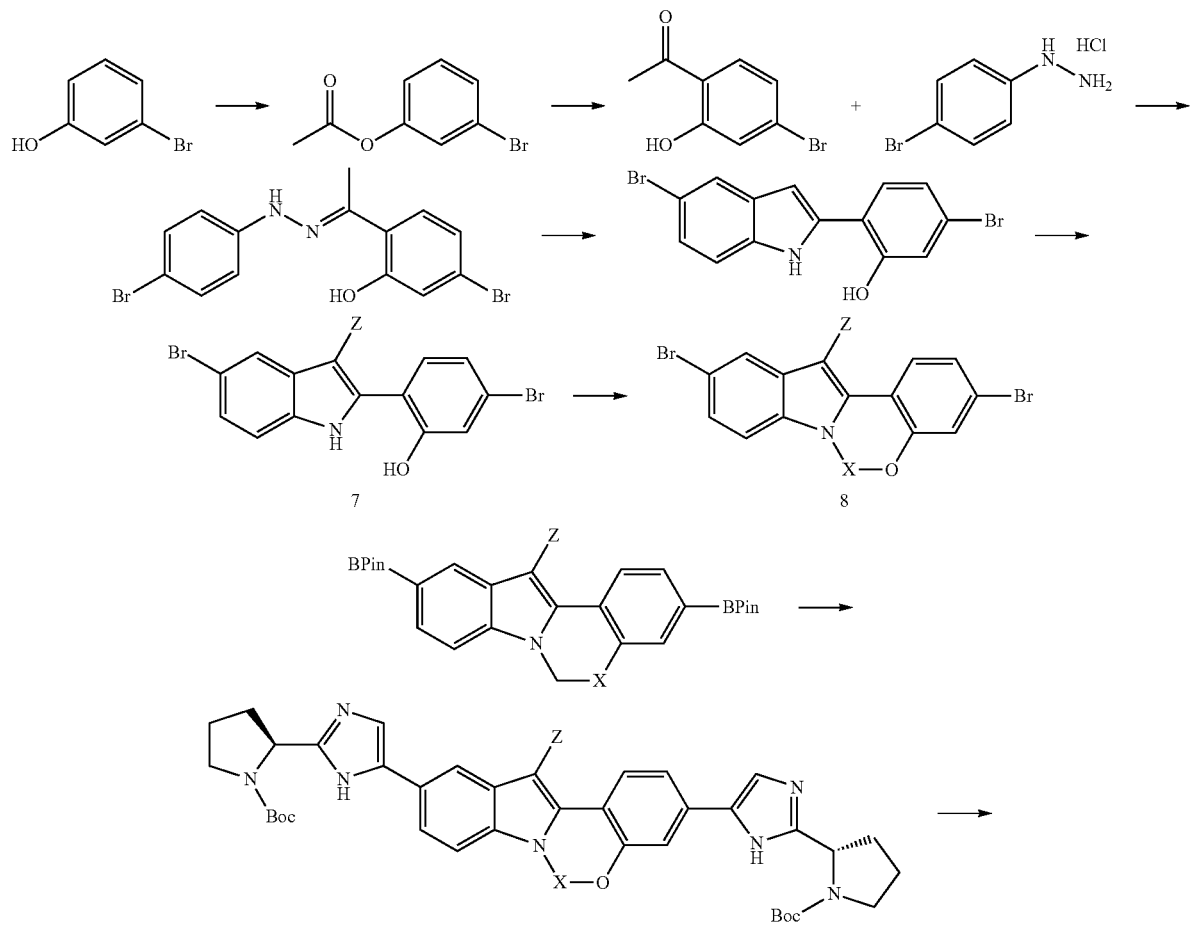

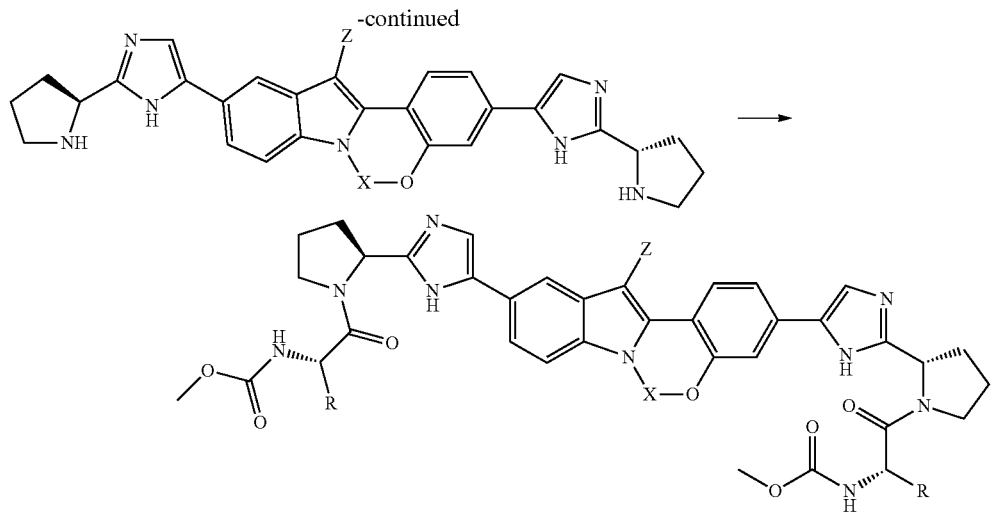

The methods described US Patent Publication No. US20120083483 are practical routes for the preparation of Compound A and related indole-based heterocyclic compounds. Nonetheless, there is always a need for alternative preparative routes which, for example, use reagents that are less expensive and/or easier to handle, consume smaller amounts of reagents, provide a higher yield of product, involve fewer steps, have smaller and/or more eco-friendly waste products, and/or provide a product of higher purity.

SUMMARY OF THE INVENTION

The present invention is directed to a process for making Compounds of Formula (I) (the "Substituted Indole Compounds"). More particularly, the present invention includes a process (alternatively referred to herein as Process P) for preparing a compound of Formula I:

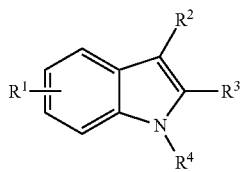

(I)

wherein said process comprises the steps:
(A) preparing a solution, wherein said solution comprises:
(a) compound of Formula (i):

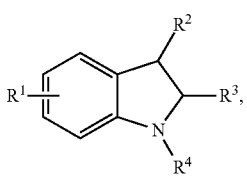

(i)

(b) a photocatalyst, or a salt thereof, (c) an oxidizing agent and (d) an organic solvent, then
(B) exposing the solution of Step A to light having a wavelength in the UV/Visible spectrum, for a time and at a temperature sufficient to provide a compound of formula (I), wherein:
$R^1$ represents up to 4 optional benzene ring substituents, which can be the same or different, and are each selected from $C_1$-$C_6$ alkyl, halo, —OTf, $C_3$-$C_7$ cycloalkyl, $C_6$-$C_{10}$ aryl, 5 or 6-membered monocyclic heteroaryl and 9 or 10-membered bicyclic heteroaryl;
$R^2$ is H or halo;
$R^3$ is selected from H, $C_1$-$C_6$ alkyl, $C_3$-$C_7$ cycloalkyl, $C_6$-$C_{10}$ aryl, 5 or 6-membered monocyclic heteroaryl, 9 or 10-membered bicyclic heteroaryl, 4 to 7-membered monocyclic heterocycloalkyl and 8 to 12-membered bicyclic heterocycloalkyl, wherein said $C_3$-$C_7$ cycloalkyl group, said $C_6$-$C_{10}$ aryl group, said 5 or 6-membered monocyclic heteroaryl group, said 9 or 10-membered bicyclic heteroaryl group, said 4 to 7-membered monocyclic heterocycloalkyl group and 8 to 12-membered bicyclic heterocycloalkyl group can be optionally substituted with one or more $R^5$ groups, which can be the same or different;
$R^4$ is selected from H, $C_1$-$C_6$ alkyl and —C(O)—($C_1$-$C_6$ alkyl), or when $R^3$ is phenyl, $R^4$ can be a group having the formula —CH($R^6$)—O—, wherein the oxygen atom of the group of formula —CH($R^6$)—O— is attached to a meta carbon atom of said $R^3$ phenyl group;
each occurrence of $R^5$ is independently selected from $C_1$-$C_6$ alkyl, halo, —OTf, $C_1$-$C_6$ haloalkyl, $C_1$-$C_6$ hydroxyalkyl, —CN, —O—($C_1$-$C_6$ alkyl), —O—($C_6$-$C_{10}$ aryl), —O—($C_1$-$C_6$ alkylene)-O—($C_1$-$C_6$ alkyl), —O—($C_1$-$C_6$ haloalkyl), —N($R^8$)$_2$, —S—($C_1$-$C_6$ alkyl), —S(O)$_2$—($C_1$-$C_6$ alkyl), —NHS(O)$_2$—($C_1$-$C_6$ alkyl), —OC(O)$R^7$, —C(O)O$R^7$, —C(O)$R^7$, —C(O)N($R^8$)$_2$, and —NHC(O)$R^7$;
$R^6$ is selected from $C_1$-$C_6$ alkyl, phenyl and 5 or 6-membered heteroaryl, wherein said heteroaryl group can be optionally substituted with $C_1$-$C_6$ alkyl or $C_3$-$C_7$ cycloalkyl;
each occurrence of $R^7$ is independently selected from H, $C_1$-$C_6$ alkyl, $C_3$-$C_7$ cycloalkyl, $C_6$-$C_{10}$ aryl and 5 or 6-membered monocyclic heteroaryl; and
each occurrence of $R^8$ is independently selected from H and $C_1$-$C_6$ alkyl.

Other embodiments, aspects and features of the present invention are either further described in or will be apparent from the ensuing description, examples, and appended claims.

DETAILED DESCRIPTION OF THE INVENTION

The present invention is directed to a process for preparing Substituted Indole Compounds of Formula (I) which are useful as HCV NS5A inhibitors. One aspect of the present invention is the process comprising Steps A and B as set forth above in the Summary of the Invention (i.e., Process P).

Definitions and Abbreviations

The term "$C_1$-$C_6$ alkyl" as used herein, refers to an aliphatic hydrocarbon group, having from 1 to 6 carbon atoms wherein one of its hydrogen atoms is replaced with a bond. A $C_1$-$C_6$ alkyl group may be straight or branched and contain. Non-limiting examples of $C_1$-$C_6$ alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. A $C_1$-$C_6$ alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, a $C_1$-$C_6$ alkyl group is linear. In another embodiment, a $C_1$-$C_6$ alkyl group is branched. Unless otherwise indicated, a $C_1$-$C_6$ alkyl group is unsubstituted.

The term "$C_6$-$C_{10}$ aryl" refers to phenyl and naphthyl. In one embodiment, an aryl group is phenyl.

The term "3 to 7-membered cycloalkyl" refers to a refers to a non-aromatic mono- or ring system comprising from about 3 to about 7 ring carbon atoms. Examples of "3 to 7-membered cycloalkyls include cyclopropyl, cyclobutyl, cyclopentyl, cyclohexyl amd cycloheptyl. In one embodiment, a 3 to 7-membered cycloalkyl group is unsubstituted. A ring carbon atom of a 3 to 7-membered cycloalkyl may be functionalized as a carbonyl group. An illustrative example of such a 3 to 7-membered cycloalkyl (also referred to herein as a "cycloalkanoyl" group) includes, but is not limited to, cyclobutanoyl:

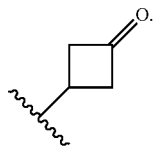 [SMILES: *C1CC(=O)C1]

The term "halo" as used herein, refers to fluorine, chlorine, bromine and iodine (alternatively referred to as fluoro, chloro, bromo, and iodo).

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 fluoro atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —$CH_2OH$, —$CH_2CH_2OH$, —$CH_2CH_2CH_2OH$ and —$CH_2CH(OH)CH_3$. The term "$C_1$-$C_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms (a "5 or 6-membered monocyclic heteroaryl"). In another embodiment, a heteroaryl group is bicyclic and has 9 or 10 ring atoms (a "9 or 10-membered bicyclic heteroaryl"). A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered monocyclic heteroaryl. In another embodiment, a heteroaryl group is a 6-membered monocyclic heteroaryl. In another embodiment, a heteroaryl group comprises a 5- to 6-membered monocyclic heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms ("3 to 7-membered monocyclic heterocycloalkyl"). In another embodiment, a heterocycloalkyl group is monocyclic has from about 4 to about 7 ring atoms ("4 to 7-membered monocyclic heterocycloalkyl"). In another embodiment, a heterocycloalkyl group is bicyclic and has from about 8 to about 12 ring atoms ("8 to 12-membered bicyclic heterocycloalkyl"). In still another embodiment, a heterocycloalkyl group is monocyclic and has 5 or 6 ring atoms ("5 or 6-membered monocyclic heterocycloalkyl"). In another embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

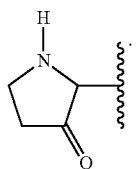 [SMILES: *C1NCCC1=O]

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic heterocycloalkyl" refers to a monocyclic heterocycloalkyl group having from 3 to 6 ring atoms. The term "4 to 7-membered monocyclic heterocycloalkyl" refers to a monocyclic heterocycloalkyl group having from 4 to 7 ring atoms. The term "7 to 11-membered bicyclic heterocycloalkyl" refers to a bicyclic heterocycloalkyl group having from 7 to 11 ring atoms. Unless otherwise indicated, a heterocycloalkyl group is unsubstituted.

Unless expressly stated to the contrary in a particular context, any of the various cyclic rings and ring systems described herein may be attached to the rest of the compound of which they are a part at any ring atom (i.e., any carbon atom or any heteroatom) provided that a stable compound results.

Unless expressly stated to the contrary, all ranges cited above are inclusive; i.e., the range includes the values for the upper and lower limits of the range as well as all values in between.

When any variable occurs more than one time in a compound involved in the process of the invention (e.g., $R^5$ or $R^7$), its definition on each occurrence is independent of its definition at every other occurrence. Also, combinations of substituents and/or variables are permissible only if such combinations result in a stable compound.

Unless expressly stated to the contrary, substitution by a named substituent is permitted on any atom in a ring (e.g., cycloalkyl, aryl, or heteroaryl) provided such ring substitution is chemically allowed and results in a stable compound.

In reference to the compounds employed as reactants or reagents in the process of the invention (e.g., Compounds (i) and (I')), a "stable" compound is one whose structure and properties remain or can be caused to remain essentially unchanged for a period of time sufficient to allow its use in the process of the invention so as to achieve the preparation of Compound of Formula (I). In reference to Compound of Formula (I), a "stable" compound is a compound which can be prepared in accordance with the process of the present invention and then isolated and whose structure and properties remain or can be caused to remain essentially unchanged for a period of time sufficient to allow use of the compound for its intended purpose; e.g., as a synthetic intermediate or for the therapeutic administration to a subject, such as a subject in need of treatment for HCV infection.

The term "salt(s)", as employed herein, denotes acidic salts formed with inorganic and/or organic acids, as well as basic salts formed with inorganic and/or organic bases. In addition, when a depicted compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of a compound, starting material or synthetic intermediate of the invention may be formed, for example, by reacting said compound, starting material or synthetic intermediate with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques.

It is also possible that the compounds, starting materials and synthetic intermediates of the invention may exist in different tautomeric forms, and all such forms are embraced within the scope of the invention. For example, all keto-enol and imine-enamine forms of the compounds, starting materials and synthetic intermediates of the invention are included in the invention.

All stereoisomers (for example, geometric isomers, optical isomers and the like) of the present compounds, starting materials and synthetic intermediates of the invention (including those of the salts, solvates, hydrates and esters thereof), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a compound, starting material or synthetic intermediate of the invention incorporates a double bond or a fused ring, both the cis- and trans-forms, as well as mixtures, are embraced within the scope of the invention.

The Process of the Present Invention

The present invention is directed to a process for preparing Substituted Indole Compounds of Formula (I) which are useful as synthetic intermediates for making HCV NS5A inhibitors. One aspect of the present invention is the process set forth above in the Summary of the Invention (i.e., Process P). The following embodiments relate to Process P.

In one embodiment, component (b) of the solution of Step A is a photocatalyst selected from an organoiridium complex or a salt thereof, an organoruthenium complex or a salt thereof, an acridine derivative or a salt thereof, a pyrylium derivative or a salt thereof, and fluorescein or a salt thereof.

In another embodiment, component (b) of the solution of Step A is an organoiridium complex or a salt thereof.

In another embodiment, component (b) of the solution of Step A is an organoruthenium complex or a salt thereof.

In one embodiment, component (b) of the solution of Step A is an organoiridium complex or a salt thereof.

In one embodiment, component (b) of the solution of Step A is selected from the following photocatalysts:

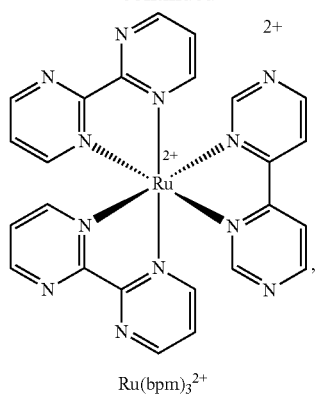

Ru(bpm)$_3^{2+}$

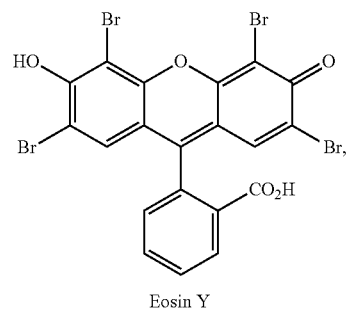

Eosin Y

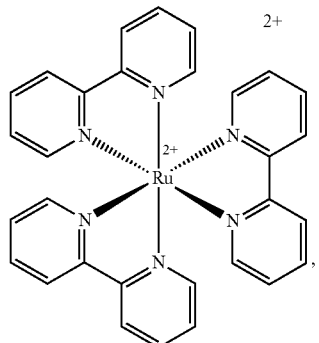

Ru(bpy)$_3^{2+}$

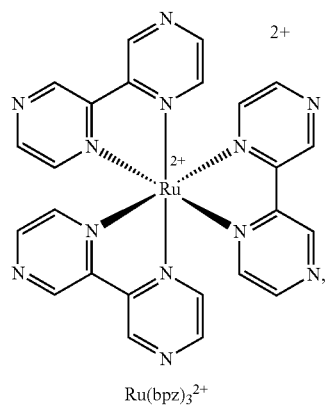

Ru(bpz)$_3^{2+}$

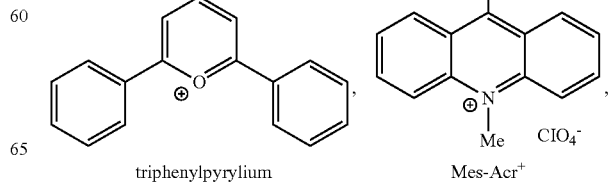

triphenylpyrylium          Mes-Acr$^+$

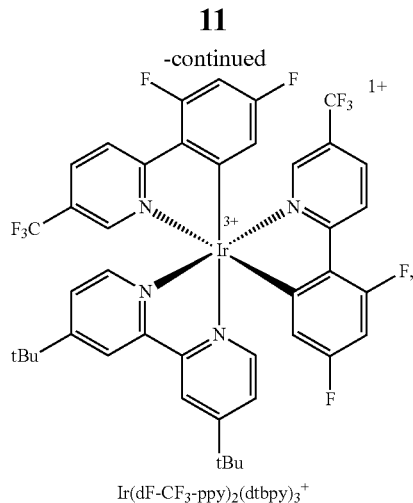

Ir(dF-CF$_3$-ppy)$_2$(dtbpy)$_3^+$

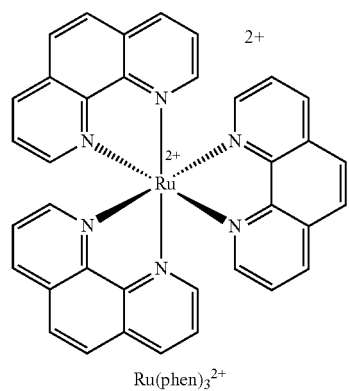

Ru(phen)$_3^{2+}$

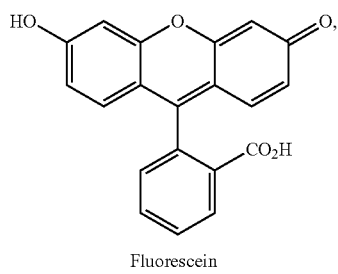

Fluorescein

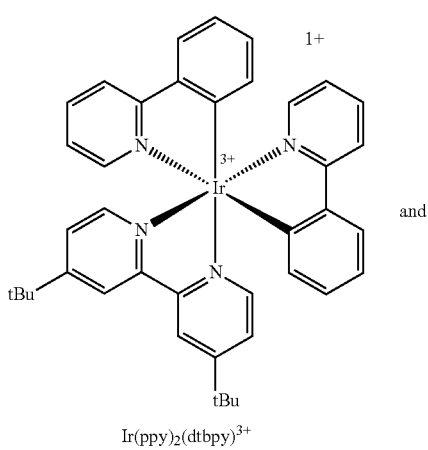

and

Ir(ppy)$_2$(dtbpy)$_3^+$

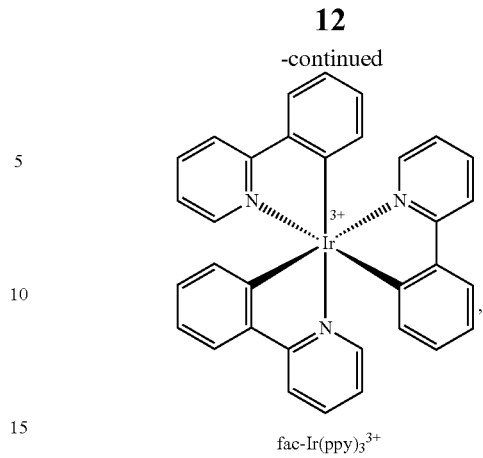

fac-Ir(ppy)$_3^{3+}$

In another embodiment, component (b) of the solution of Step A is an organoiridium complex selected from fac-Ir(ppy)$_3$, fac-Ir(dF-ppy)$_3$, Ir(ppy)$_2$(dtbpy), Ir(ppy)$_3$ and Ir(dF-CF$_3$-ppy)$_2$(dtbpy), or a salt thereof.

In another embodiment, component (b) of the solution of Step A is [Ir(dF-CF$_3$-ppy)$_2$(dtbpy)](PF$_6$).

In another embodiment, component (b) of the solution of Step A is an organoruthenium complex selected from [Ru(bpm)$_3$]Cl$_2$, [Ru(bpy)$_3$]Cl$_2$, [Ru(bpz)$_3$]Cl$_2$ and [Ru(phen)]Cl$_2$.

In one embodiment, component (c) of the solution of Step A is selected from an organic peroxyester, an organic peroxide, an organic carbonoperoxoate and an inorganic persulfate.

In another embodiment, component (c) of the solution of Step A is an organic peroxyester.

In another embodiment, component (c) of the solution of Step A is an organic peroxide.

In another embodiment, component (c) of the solution of Step A is an organic carbonoperoxoate.

In one embodiment, component (c) of the solution of Step A is tert-butyl peroxybenzoate.

In one embodiment, component (d) of the solution of Step A is selected from acetonitrile, N,N-dimethylformamide, N,N-dimethylacetamide and dimethylsulfoxide.

In another embodiment, component (d) of the solution of Step A is N,N-dimethylacetamide.

In one embodiment, in Step B, the UV-visible light has a wavelength of from 350 nm to 500 nm.

In another embodiment, in Step B, the UV-visible light has a wavelength of from 430-450 nm.

In one embodiment, in Step B, the solution of Step A is exposed to the UV-visible light for a time period of from 10 minutes to 2 hours.

In another embodiment, in Step B, the solution is exposed to the UV-visible light for a time period of from 30 minutes to 1 hour.

In one embodiment, the solution of Step A is maintained at a temperature of from −20° C. to 25° C. throughout the entirety of Step B.

In another embodiment, the solution of Step A is maintained at a temperature of from −10° C. to 10° C. throughout the entirety of Step B.

In one embodiment, the compounds of formulas (i) and (I), each occurrence of R$^1$ is selected from halo.

In another embodiment, for the compounds of formulas (i) and (I), R$^2$ is H.

In another embodiment, for the compounds of formulas (i) and (I), R$^3$ is phenyl and R$^4$ is —CH(R$^6$)—O—, wherein the oxygen atom of the group of formula —CH(R$^6$)—O— is attached to a meta carbon atom of said phenyl group.

In still another embodiment, for the compounds of formulas (i) and (I), R$^4$ is selected from H, C$_1$-C$_6$ alkyl and —C(O)—(C$_1$-C$_6$ alkyl).

In one embodiment, the compound of formula (i) has the formula (i'):

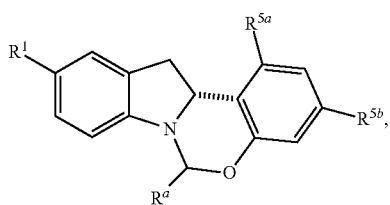

(i')

and the compound of formula (I) has the formula (I'):

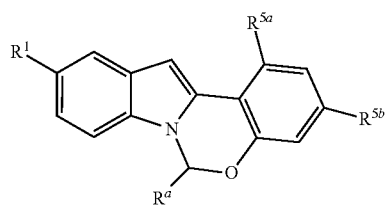

(I')

wherein R$^1$ and R$^{5b}$ are each halo, R$^{5a}$ is H or F, and R$^a$ is phenyl or 5 or 6-membered heteroaryl, wherein said heteroaryl group is optionally substituted with C$_1$-C$_6$ alkyl or C$_3$-C$_7$ cycloalkyl.

In another embodiment, for the compounds of formulas (I') and (i'), R$^1$ and R$^{5b}$ are each Br, R$^{5a}$ is H, and R$^a$ is phenyl.

In another embodiment, for the compounds of formulas (I') and (i'), R$^1$ and R$^{5b}$ are each Br, R$^{5a}$ is F, and R$^a$ is thiazolyl, optionally substituted with a cyclopropyl group.

In one embodiment, the compound of formula (I) made using Process P is a compound of formula (I'):

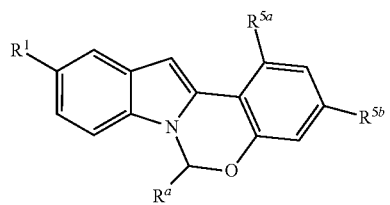

(I')

wherein R$^1$ and R$^{5b}$ are each halo, R$^{5a}$ is H or F, and R$^a$ is phenyl or 5 or 6-membered heteroaryl, wherein said heteroaryl group is optionally substituted with C$_1$-C$_6$ alkyl or C$_3$-C$_7$ cycloalkyl.

In one embodiment, the compound of formula (I) made using Process P is:

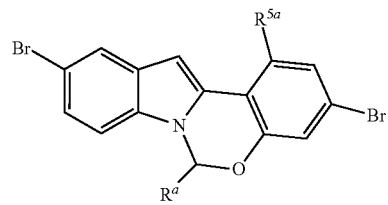

wherein
R$^a$ is phenyl or 5-membered heteroaryl, and said 5-membered heteroaryl is optionally substituted with C$_1$-C$_6$ alkyl or C$_3$-C$_7$ cycloalkyl; and
R$^{5a}$ is H or F.

In another embodiment, the compound of formula (I) made using Process P is:

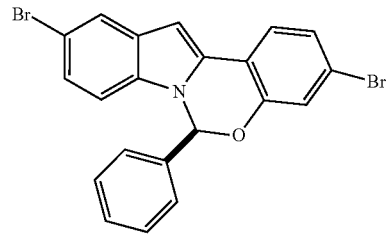 [SMILES: Brc1ccc2c(c1)O[C@@H](c1ccccc1)n1c-2cc2cc(Br)ccc21]

In another embodiment, the compound of formula (I) made using Process P is:

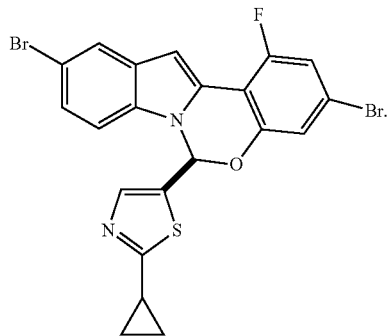 [SMILES: Fc1cc(Br)cc2c1-c1cc3cc(Br)ccc3n1[C@H](c1cnc(C3CC3)s1)O2]

In one embodiment, any step of Process P can be conducted in any organic solvent.

EXAMPLES

General Methods

Solvents, reagents, and intermediates that are commercially available were used as received. Reagents and intermediates that are not commercially available were prepared in the manner as described below. $^1$H NMR spectra were obtained on a Bruker Avance 500 (500 MHz) and are reported as ppm downfield from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 minutes—10% CH$_3$CN, 5 minutes—95% CH$_3$CN, 5-7 minutes—95% CH$_3$CN, 7 minutes—stop. The retention time and observed parent ion are given. Flash column chromatography was performed using pre-packed normal phase silica from Biotage, Inc. or bulk silica from Fisher Scientific. Unless otherwise indicated, column chromatography was performed using a gradient elution of hexanes/ethyl acetate, from 100% hexanes to 100% ethyl acetate.

Example 1

Preparation of Compound 2

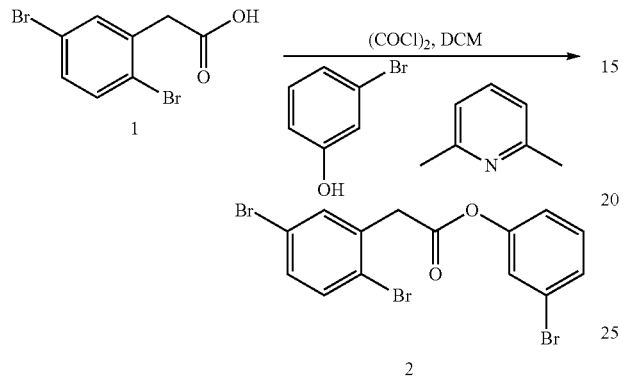

A 2 L 3-neck round-bottomed flask equipped with an overhead stirrer and a nitrogen inlet was charged with compound 1 (100 g, 339 mmol) and dichloromethane (1200 mL, 12 vol) at room temperature. To the resulting solution was added N,N-dimethylformamide (1.24 g, 0.05 equiv), followed by slow addition of oxalyl chloride (48.3 g, 1.1 equiv) over a 20 minute period. The resulting reaction was allowed to stir under nitrogen at room temperature for 1 hour and monitored by HPLC for complete conversion. After the reaction was complete, the reaction mixture volume was concentrated to 500 mL and held for further use.

A separate 2 L 3-neck round-bottomed flask equipped with an overhead stirrer and a nitrogen inlet was charged with 3-bromophenol (62.9 g, 356 mmol, 1.05 equiv) and dichloromethane (530 mL, 5 vol). To the resulting solution was added 2,6-Lutidine (73.5 g, 2.0 equiv) while maintaining the reaction temperature below 25° C., and the resulting reaction was then cooled to 5° C. The reaction mixture containing compound 1 was then added slowly while maintaining reaction temperature between 0 and 5° C. The resulting reaction was allowed to stir for 1 hour and monitored by HPLC for complete conversion of compound 1 to compound 2.

After the reaction was complete, the reaction was quenched with 1N HCl solution (530 mL). The aqueous layer was cut, and the organic phase was washed with water (530 mL). The volume of the organic phase was then concentrated in vacuo to 300 mL and dichloromethane was replaced with acetonitrile via continuous distillation. During the solvent swap, the resulting solution of compound 2 became a slurry. Water (318 mL) was added slowly to the slurry over 30 minutes, and the resulting slurry was allowed to stir for 60 minutes at room temperature. The slurry was then filtered and the collected solid was washed with 50% acetonitrile/water (318 mL). After drying under vacuum and nitrogen sweeping, 146.0 g (91% yield) of compound 2 was obtained as a white crystalline solid. $^1$H NMR (CDCl$_3$, 400 MHz): δ=7.54 (d, J=3.0 Hz, 1H), 7.49 (d, J=10.6 Hz, 1H), 7.39 (dd, J=10.0, 2.4 Hz, 1H), 7.35-7.32 (m, 2H), 7.25 (d, J=10.1 Hz, 1H), 7.10 (dd, J=10.6, 1.6 Hz, 1H), 4.00 (s, 2H).

Example 2

Preparation of Compound 3

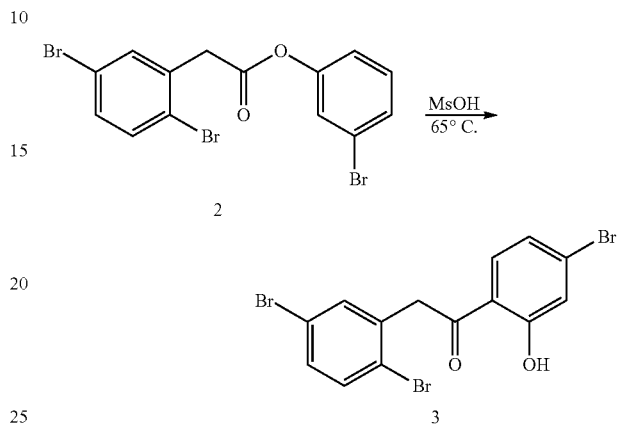

A 2 L 3-neck round-bottomed flask equipped with an overhead stirrer and a nitrogen inlet was charged with methanesulfonic anhydride (10.61 g, 59.1 mmol, 0.2 equiv) and methanesulfonic acid (384 mL, 20 equiv) at room temperature. The resulting mixture was heated to 90° C. and allowed to stir at this temperature for 1 hour. The reaction mixture was then cooled to 65° C., and compound 2 (132.5 g, 295 mmol) was added under nitrogen and the resulting reaction was allowed to stir for 24 hours at 65° C. The reaction was cooled to room temperature and a mixture of isopropanol/water (3:1, 1115 ml, 8× vol) was added while maintaining reaction temperature below 50° C. The resulting slurry was then heated to 90° C. and allowed to stir at this temperature for 20 minutes, then and filtered. The collected solid was washed with a mixture of isopropanol/water (1:1, 418 mL), then dried under vacuum and nitrogen sweeping at 60 to 70° C. for 12 hours, to provide compound 3 as a white crystalline solid (108.0 g, 82%). $^1$H NMR (500 MHz, DMSO-d$_6$): δ=11.60 (s, 1H), 7.87 (d, J=8.5 Hz, 1H), 7.67 (d, J=2.4 Hz, 1H), 7.59 (d, J=8.7 Hz, 1H), 7.45 (dd, J=8.7, 2.4 Hz, 1H), 7.26 (d, J=1.9 Hz, 1H), 7.20 (dd, J=8.4, 1.8 Hz, 1H), 4.59 (s, 2H).

Example 3

Preparation of Compound 4

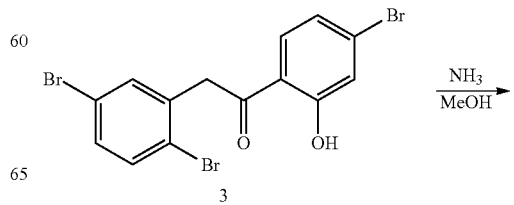

-continued

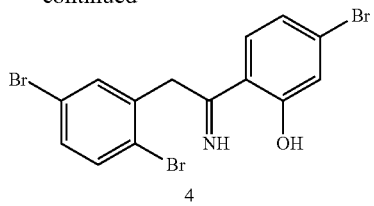

A 500 mL round-bottomed flask equipped with an overhead stirrer and a nitrogen inlet was charged with compound 3 (37.1 g., 83 mmol) and 7N ammonia in methanol solution (201 mL, 1.405 mol, 17 equiv). The resulting reaction was allowed to stir vigorously under nitrogen at room temperature for 20 hours. The resulting suspension was filtered and the collected yellow crystalline solid was rinsed with a minimal amount of methanol (mother liquor loss=1.92 g. or 5.2%), then dried with a nitrogen sweep to <1 wt % methanol to provide compound 4 (33.6 g., 91% yield), which was used without further purification. $^1$H NMR (CDCl$_3$, 400 MHz): δ=9.97, (s, 1H), 7.56 (d, J=9.1 Hz, 1H), 7.48 (d, J=8.6 Hz, 1H), 7.42 (d, J=2.4 Hz, 1H), 7.40 (d, J=2.4 Hz, 1H), 7.22 (d, J=2.0 Hz, 1H), 7.02 (dd, J=8.6, 2.0 Hz, 1H), 4.22 (s, 2H).

Example 4

Preparation of Compound 5

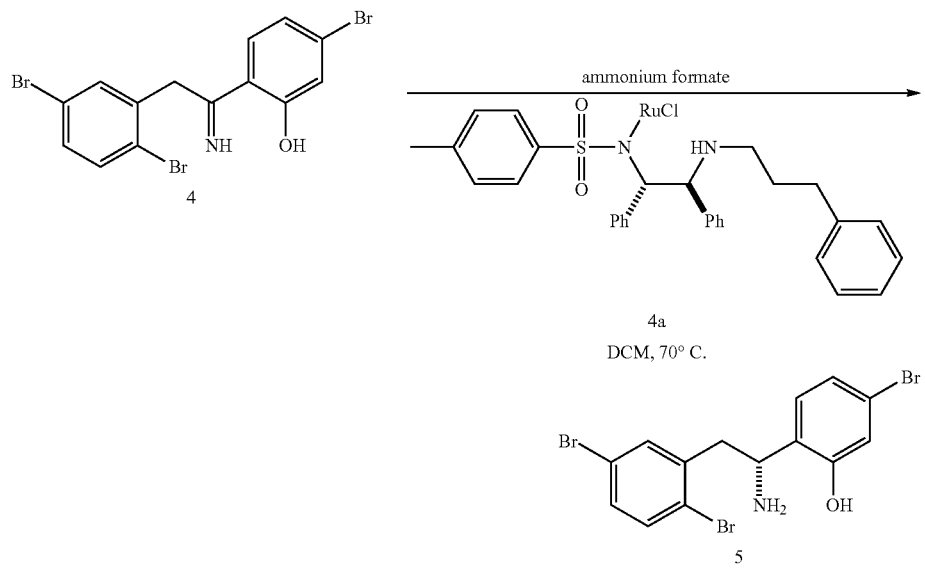

A 1 L Parr shaker was charged with compound 4 (38.8 g., 87 mmol), ammonium formate (10.92 g., 173 mol, 2.0 equiv), and compound 4a (161 mg, 0.260 mmol, 0.3 mol %, 0.003 equiv), and the reaction vessel was purged with nitrogen for 10 minutes. Separately, dichloromethane (427 mL, 11 vol) was degassed with nitrogen then added under nitrogen to the solution containing compound 4. The resulting reaction was heated to 70° C. and allowed to stir at this temperature under nitrogen atmosphere for 24 hours. The reaction mixture was cooled to room temperature and neutralized to pH 7.5 using 10% aqueous NaHCO$_3$ solution. The aqueous layer was cut, and the organic phase was washed with water (2×30 mL). The organic phase was then concentrated in vacuo, solvent switched to acetonitrile (194 mL, 5 vol), then seeded with compound 5. After 1 hour of stirring the formation of a seed bed was verified, then water (155 mL) was added slowly to the seed bed over 1 hour. The resulting crystals were collected by filtration and dried under a nitrogen sweep, to provide compound 5 as a white solid (33.1 g., 73.6 mmol, 85% yield, 99% ee). $^1$H NMR (CDCl$_3$, 400 MHz): δ=7.46 (d, J=8.4 Hz, 1H), 7.27 (m, 1H), 7.22 (d, J=2.4 Hz, 1H), 7.06 (d, J=1.9 Hz, 1H), 6.87 (dd, J=8.1, 2.0 Hz, 1H), 6.70 (d, J=8.1 Hz, 1H), 4.45 (dd, J=8.8, 5.7 Hz, 1H), 3.15 (m, 2H).

Example 5

Preparation of Compound 6

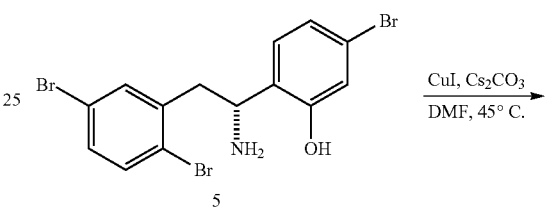

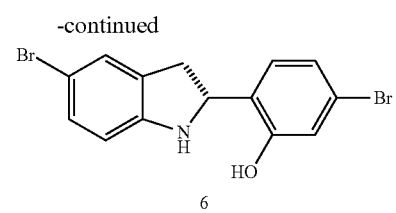

A 500 mL round-bottomed flask equipped with a magnetic stir bar, a thermocouple, and a nitrogen inlet was charged with compound 5 (33.0 g., 73.3 mmol), copper iodide (698 mg., 3.67 mmol, 0.05 equiv) and cesium carbonate (47.8 g., 147 mmol, 2.0 equiv), and the flask was purged with nitrogen for 10 minutes. In a separate flask, N,N-dimethylformamide (165 mL, 5.0 vol) was sparged with nitrogen for 30 minutes, then added to the solution of compound 5 via cannula, under nitrogen. The resulting reaction was heated to 45° C. and allowed to stir at this temperature for 1 hour. The reaction mixture was then cooled to room temperature and diluted with 20 volumes ethyl acetate (100 mL) and immediately neutralized with 25 wt % aqueous ammonium chloride with vigorous stirring. The resulting solution was adjusted to pH 7.5 using 1N HCl. The aqueous layer was cut, and back-extracted with 2 volumes ethyl acetate, and the combined organics were washed sequentially with 4 volumes of 10 wt % aqueous sodium chloride and 4 volumes of water. The organics were then concentrated with a continuous solvent switch to acetonitrile (target final volume of 5 volumes acetonitrile, <5% residual ethyl acetate). During the solvent switch, white crystals of 6 were observed to precipitate forming a seed bed. When the target volume was reached, 5 volumes of water was added slowly over 60 minutes with stirring. When the water addition was complete, the slurry was allowed to stir for an additional 1 hour, then the solids were collected by filtration and washed with 1 volume of 1:1 acetonitrile:water, then dried via nitrogen sweep, to provide compound 6 as a white crystalline solid (24.6 g., 66.7 mmol, 91% yield, 99% ee). $^1$H NMR (CDCl$_3$, 400 MHz): δ=9.58 (s, 1H), 7.31 (s, 1H), 7.25 (d, J=8.3 Hz, 1H), 7.10 (d, J=2.0 Hz, 1H), 6.98 (dd, J=8.0, 2.0 Hz, 1H), 6.90 (d, J=8.0 Hz, 1H), 6.73 (d, J=8.0 Hz, 1H), 4.94 (m, 1H), 4.40 (s, 1H), 3.30 (t, J=8.6 Hz, 1H), 3.10 (dd, J=15.7, 12.4 Hz, 1H).

Example 6

Preparation of Compound 7 added to the reaction mixture, followed by slow addition of water (58 mL). The resulting mixture was agitated at 20-25° C. for another 3 hours, then the reaction was filtered and the collected solid was washed sequentially with 87 mL (3 vol) acetonitrile:water (2:1) followed by 58 mL (2 vol) of water. The solid was then dried under a nitrogen sweep, to provide compound 7 as a white solid (33.4 g., 73.1 mmol, 93% yield). $^1$H NMR (CDCl$_3$, 400 MHz): δ=7.58 (m, 2H), 7.40-7.36 (m, 4H), 7.23 (s, 1H), 7.08 (d, J=2.0 Hz, 1H), 6.98 (dd, J=8.2, 2.0 Hz, 1H), 6.82 (m, 2H), 6.76 (s, 1H), 4.71 (d, J=8.9 Hz, 1H), 3.52 (dd, J=15.7, 8.9 Hz, 1H), 3.12 (d, J=15.7 Hz, 1H).

Example 7

Preparation of Compound 8

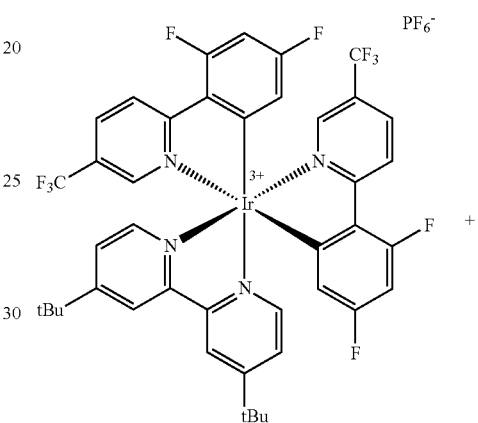

7a

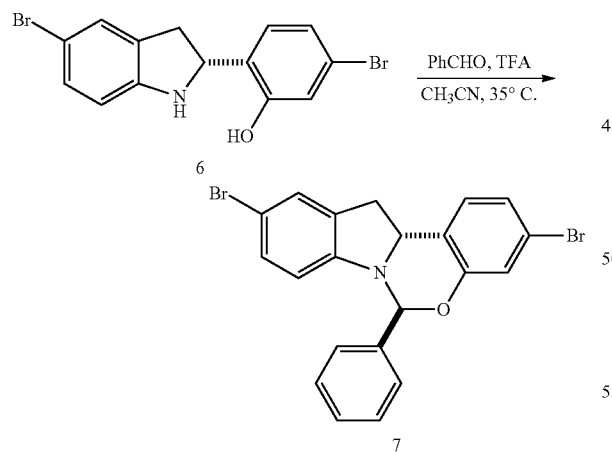

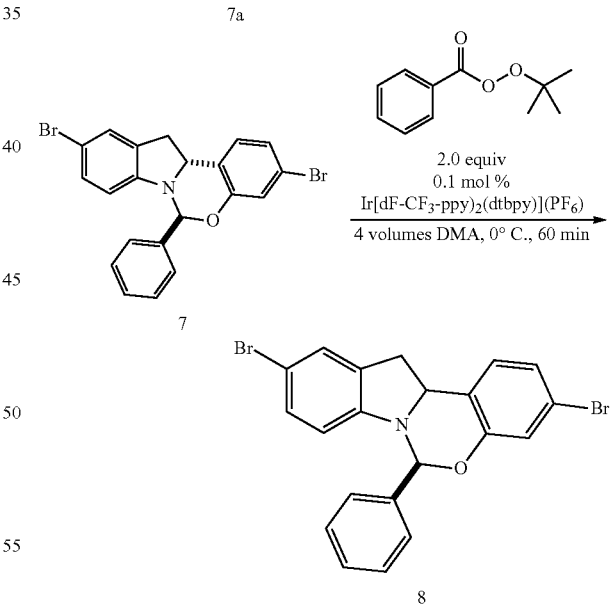

To a suspension of compound 6 (29.0 g., 79.0 mmol) and benzaldehyde (11.15 mL, 110 mmol, 1.4 eq) in acetonitrile (116 mL, 4 vol), under nitrogen atmosphere, was added trifluoroacetic acid (0.303 mL, 0.05 eq). The resulting reaction was heated to 35° C. and allowed to stir at this temperature for 3 hours during which time crystallization of the product was observed. The slurry was cooled to 20-25° C. and held at this temperature for 1 hour. A 5% aqueous sodium bicarbonate solution (13.2 mL, 0.1 eq) was then Compound 7 (100 g, 219 mmol) was added to a 1 liter jacketed round bottom flask followed by Compound 7a (249 mg, 0.219 mmol, 0.1 mol %), N,N-dimethylacetamide (400 mL, 4 volumes) and tert-butylperoxybenzoate (82 mL, 437 mmol, 2.0 equiv). The resulting reaction was put under a nitrogen atmosphere and allowed to stir at room temperature until complete dissolution was achieved, at which point the solution was sparged with nitrogen while being cooled to −5° C. using a glycol/water bath. The cooled reaction mixture was then passed at a rate of 2.5 mL/min through a reactor consisting of 100 linear feet of perfluoroalkoxy (PFA) tubing (⅛" internal diameter) surrounded by blue light-emitting diodes ("LEDs") ($\lambda_{max}$ 440 nm), wherein the internal temperature of the reactor had been precooled to −5° C. The internal reaction volume of the reactor was ~150 ml, providing a residence time of 60 minutes at the 2.5 mL/min flow rate. The reaction stream was collected in a 1 liter jacketed round bottom flask that was precooled to −5° C. The total time required to process the entire reaction volume through the LED reactor was about 5 hours. When the entire reaction volume was collected, Na₂SO₃ aqueous solution (5.51 g, 0.2 eq., in 24 mL of water) was added to the crude reaction mixture over a period of 30 minutes. The resulting solution was seeded with pure compound 8 (50 mg, 0.05%) and the resulting mixture was allowed to age for 20 minutes. To the resulting slurry was added, over a 2 hour period, an aqueous solution comprising Na₂SO₃ (5.51 g Na₂SO₃, 0.2 equiv) and LiOH (19.3 g LiOH, 2.1 equiv) in water (97 mL). Upon completion of this addition, additional water (55 mL) was added over a 1 hour period. The resulting solution was filtered and the collected solid was washed sequentially with a mixture of N,N-dimethylacetamide/water (60/40, v/v, 2×150 mL), water(2×150 mL), and isopropanol (2×150 mL). The washed solid was then dried under vacuum with nitrogen sweep for 15 hours to provide compound 8 (85.8 g, 84.5% isolated yield). ¹H NMR (CDCl₃, 400 MHz): δ=7.81 (d, J=1.8 Hz, 1H), 7.51 (d, J=8.1 Hz, 1H), 7.37-7.28 (m, 3H), 7.21-7.17 (m, 3H), 7.11-7.08 (m, 3H), 6.85 (s, 1H), 6.70 (d, J=8.8 Hz, 1H), 6.90 (d, J=8.0 Hz, 1H), 6.73 (d, J=8.0 Hz, 1H), 4.94 (m, 1H), 4.40 (s, 1H), 3.30 (t, J=8.6 Hz, 1H), 3.10 (dd, J=15.7, 12.4 Hz, 1H).

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entirety into the disclosure.

What is claimed is:

1. A process for preparing a compound of Formula (I):

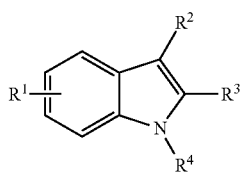

(I)

wherein said process comprises the steps:
(A) preparing a solution, wherein said solution comprises: (a) compound of Formula (i):

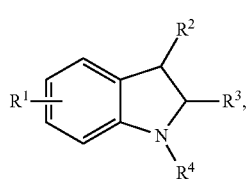

(i)

(b) a photocatalyst, selected from fac-Ir(ppy)₃, fac-Ir(dF-ppy)₃, Ir(ppy)₂(dtbpy), [Ir(dF-CF₃-ppy)₂(dtbpy)(PF₆), Ir(ppy)₃, Ir(dF-CF₃-ppy)₂(dtbpy), [Ru(bpm)₃]Cl₂, [Ru(bpy)₃]Cl₂, [Ru(bpz)₃]Cl₂ and [Ru(phen)]Cl₂, or a salt thereof, (c) an oxidizing agent, selected from an organic peroxyester, and (d) an organic solvent, selected from acetonitrile, N,N-dimethylformamide, N,N-dimethylacetamide and dimethylsulfoxide;

(B) exposing the solution of Step A to light having a wavelength in the UV/Visible spectrum, for a time and at a temperature sufficient to provide a compound of formula (I), wherein:
$R^1$ represents up to 4 optional benzene ring substituents, which can be the same or different, and are each selected from $C_1$-$C_6$ alkyl, halo, —OTf, $C_3$-$C_7$ cycloalkyl, $C_6$-$C_{10}$ aryl, 5 or 6-membered monocyclic heteroaryl and 9 or 10-membered bicyclic heteroaryl;

$R^2$ is H or halo;

$R^3$ is selected from H, $C_1$-$C_6$ alkyl, $C_3$-$C_7$ cycloalkyl, $C_6$-$C_{10}$ aryl, 5 or 6-membered monocyclic heteroaryl, 9 or 10-membered bicyclic heteroaryl, 4 to 7-membered monocyclic heterocycloalkyl and 8 to 12-membered bicyclic heterocycloalkyl, wherein said $C_3$-$C_7$ cycloalkyl group, said $C_6$-$C_{10}$ aryl group, said 5 or 6-membered monocyclic heteroaryl group, said 9 or 10-membered bicyclic heteroaryl group, said 4 to 7-membered monocyclic heterocycloalkyl group and 8 to 12-membered bicyclic heterocycloalkyl group can be optionally substituted with one or more $R^5$ groups, which can be the same or different;

$R^4$ is selected from H, $C_1$-$C_6$ alkyl and C(O)—($C_1$-$C_6$ alkyl), or when $R^3$ is phenyl, $R^4$ can be a group having the formula CH($R^6$)—O—, wherein the oxygen atom of the group of formula —CH($R^6$)—O— is attached to a meta carbon atom of said $R^3$ phenyl group;

each occurrence of $R^5$ is independently selected from $C_1$-$C_6$ alkyl, halo, —OTf, $C_1$-$C_6$ haloalkyl, $C_1$-$C_6$ hydroxyalkyl, —CN, —O—($C_1$-$C_6$ alkyl), —O—($C_6$-$C_{10}$ aryl), —O—($C_1$-$C_6$ alkylene)-O—($C_1$-$C_6$ alkyl), —O—($C_1$-$C_6$ haloalkyl), —N($R^8$)₂, —S—($C_1$-$C_6$ alkyl), —S(O)₂—($C_1$-$C_6$ alkyl), —NHS(O)₂—($C_1$-$C_6$ alkyl), —OC(O)$R^7$, —C(O)O$R^7$, —C(O)$R^7$, —C(O)N($R^8$)₂, and —NHC(O)$R^7$;

$R^6$ is selected from $C_1$-$C_6$ alkyl, phenyl and 5 or 6-membered heteroaryl, wherein said heteroaryl group can be optionally substituted with $C_1$-$C_6$ alkyl or $C_3$-$C_7$ cycloalkyl;

each occurrence of $R^7$ is independently selected from H, $C_1$-$C_6$ alkyl, $C_3$-$C_7$ cycloalkyl, $C_6$-$C_{10}$ aryl and 5 or 6-membered monocyclic heteroaryl; and each occurrence of $R^8$ is independently selected from H and $C_1$-$C_6$ alkyl.

2. The process of claim 1, wherein the organic peroxyester is tert-butyl peroxybenzoate.

3. The process of claim 1, wherein in Step B, the UV-visible light has a wavelength of from 350 nm to 500 nm.

4. The process of claim 1, wherein in Step B, the solution is exposed to the UV-visible light for a time period of from 10 minutes to 2 hours.

5. The process of claim 1, wherein in Step B, the solution is exposed to the UV-visible light for a time period of from 30 minutes to 1 hour.

6. The process of claim 1, wherein the solution of Step A is maintained at a temperature of from −20° C. to 25° C. throughout the entirety of Step B.

7. The process of claim 1, wherein for the compounds of formulas (i) and (I), $R^1$ is halo.

8. The process of claim 1, wherein for the compounds of formulas (i) and (I), $R^2$ is H.

9. The process of claim 1, wherein for the compounds of formulas (i) and (I), $R^3$ is phenyl and $R^4$ is —CH($R^6$)—O—, wherein the oxygen atom of the group of formula —CH($R^6$)—O— is attached to a meta carbon atom of said phenyl group.

10. The process of claim 1, wherein for the compounds of formulas (i) and (I), $R^4$ is selected from H, $C_1$-$C_6$ alkyl and —C(O)—($C_1$-$C_6$ alkyl).

11. The process of claim 1, wherein the compound of formula (i) has the formula (i'):

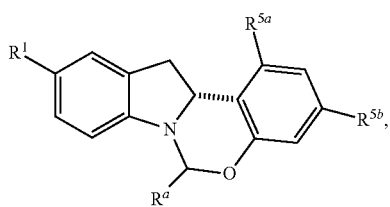

(i')

and the compound of formula (I) has the formula (I'):

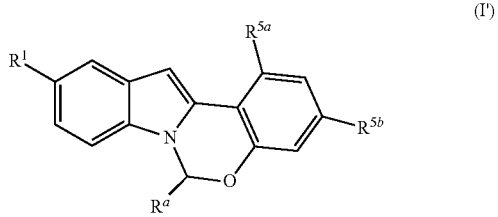

(I')

wherein $R^1$ and $R^{5b}$ are each halo, $R^{5a}$ is H or F, and $R^a$ is phenyl or 5 or 6-membered heteroaryl, wherein said heteroaryl group is optionally substituted with $C_1$-$C_6$ alkyl or $C_3$-$C_7$ cycloalkyl.

12. The process of claim 11, wherein $R^1$ and $R^{5b}$ are each Br, $R^{5a}$ is H, and $R^a$ is phenyl.

13. The process of claim 11, wherein $R^1$ and $R^{5b}$ are each Br, $R^{5a}$ is F, and $R^a$ is thiazolyl, optionally substituted with a cyclopropyl group.

* * * * *